United States Patent
Kihara et al.

(10) Patent No.: US 10,266,693 B2
(45) Date of Patent: Apr. 23, 2019

(54) HIGH STRENGTH SILICONE ELASTOMERS AND COMPOSITIONS THEREFOR

(71) Applicant: NuSil Technology LLC, Carpinteria, CA (US)

(72) Inventors: Matthew Kihara, Boise, ID (US); James Lambert, Carpinteria, CA (US)

(73) Assignee: NuSil Technology LLC, Carpinteria, CA (US)

( * ) Notice: Subject to any disclaimer, the term of this patent is extended or adjusted under 35 U.S.C. 154(b) by 96 days.

(21) Appl. No.: 15/185,490

(22) Filed: Jun. 17, 2016

(65) Prior Publication Data

US 2016/0369100 A1 Dec. 22, 2016

Related U.S. Application Data

(60) Provisional application No. 62/181,712, filed on Jun. 18, 2015.

(51) Int. Cl.
| | | |
|---|---|---|
| *C08L 83/04* | (2006.01) | |
| *C08K 9/06* | (2006.01) | |
| *C09C 1/30* | (2006.01) | |
| *A61L 27/44* | (2006.01) | |
| *C09D 183/04* | (2006.01) | |
| *C08K 3/36* | (2006.01) | |
| *C08K 5/56* | (2006.01) | |
| *C08K 9/04* | (2006.01) | |
| *C08L 83/00* | (2006.01) | |
| *C08G 77/12* | (2006.01) | |
| *C08G 77/62* | (2006.01) | |
| *C08G 77/20* | (2006.01) | |

(52) U.S. Cl.
CPC ............ *C08L 83/04* (2013.01); *A61L 27/446* (2013.01); *C08K 3/36* (2013.01); *C08K 5/56* (2013.01); *C08K 9/04* (2013.01); *C08K 9/06* (2013.01); *C08L 83/00* (2013.01); *C09C 1/3081* (2013.01); *C09D 183/04* (2013.01); *A61L 2430/04* (2013.01); *C08G 77/12* (2013.01); *C08G 77/20* (2013.01); *C08G 77/62* (2013.01)

(58) Field of Classification Search
CPC ...... C08K 5/5425; C08L 83/04; C09D 183/04
USPC ........................................................ 524/588
See application file for complete search history.

(56) References Cited

U.S. PATENT DOCUMENTS

| | | | |
|---|---|---|---|
| 3,884,886 A | | 5/1975 | Plueddemann |
| 4,162,243 A | | 7/1979 | Lee et al. |
| 4,418,165 A | * | 11/1983 | Polmanteer .............. G02B 1/04 523/107 |
| 5,563,211 A | * | 10/1996 | Kosal ....................... C08K 9/06 524/731 |
| 5,908,878 A | | 6/1999 | Baity et al. |
| 6,372,860 B1 | * | 4/2002 | Miyoshi .................. C08L 83/04 264/331.11 |
| 2011/0251321 A1 | * | 10/2011 | Zhu ......................... C08L 83/04 524/314 |
| 2013/0011617 A1 | * | 1/2013 | Tasaki ..................... B29C 45/14 428/148 |
| 2014/0018464 A1 | * | 1/2014 | Senoo .................... A61L 29/042 523/105 |

FOREIGN PATENT DOCUMENTS

| | | |
|---|---|---|
| EP | 2679636 A1 | 1/2014 |
| EP | 2845880 A1 | 3/2015 |
| WO | 2013/137473 A1 | 9/2013 |

OTHER PUBLICATIONS

International Preliminary Report from corresponding PCT Application No. PCT/US2016/037801, pp. 1-11, dated Dec. 19, 2017.

\* cited by examiner

*Primary Examiner* — Marc S Zimmer
(74) *Attorney, Agent, or Firm* — Hoffmann & Baron, LLP

(57) ABSTRACT

Compositions for forming a silicone elastomer and the silicone elastomers thereby which have improved characteristics and which can be used for medical devices are disclosed. The composition for forming a silicone elastomer can include (A) an organopolysiloxane having silicon-bonded alkenyl groups; (B) an organohydrogensiloxane having an average of two or more silicon-bonded hydrogen atoms in the molecule; (C) an inorganic filler; and (D) a filler treatment agent which includes an alkenyl-containing group, e.g., an alkenyl-containing organosilane or organosilazane.

16 Claims, No Drawings

HIGH STRENGTH SILICONE ELASTOMERS AND COMPOSITIONS THEREFOR

CROSS-REFERENCE TO RELATED APPLICATION

This application claims the benefit of U.S. Provisional Application No. 62/181,712 filed Jun. 18, 2015, the entire disclosure of which is hereby incorporated by reference herein.

TECHNICAL FIELD

The present disclosure relates to silicone elastomer compositions and products therefrom which are suitable for use in medical devices such as breast implants, medical balloons and medical tubes.

BACKGROUND

Silicone elastomers find wide applicability due to their varied and desirable properties. Silicone elastomers can be prepared from compositions including organopolysiloxanes having alkenyl groups, organohydrogenpolysiloxanes, catalysts and optionally inorganic fillers.

For example, WO2013/137473 relates to silicone elastomer compositions and elastic material for medical devices and medical tubes. This publication discloses elastomer compositions including organopolysiloxanes having alkenyl groups, organohydrogenpolysiloxanes, inorganic fillers and catalysts. The cured products are characterized as having hardness of 40 or greater, a breaking elongation of 500% or greater, no yield point and a tensile strength of 7.0 MPa or greater. The tensile strength is particularly preferably from 8.25 to 14.0 MPa. The silicone elastomeric products are disclosed for use in medical tubes, among other uses.

However, a continuing need exists for silicone elastomers having appropriate properties for medical device applications, among others.

SUMMARY OF THE DISCLOSURE

Advantages of the present disclosure include compositions for forming a silicone elastomer and the silicone elastomers therefrom which have improved characteristics and which can be used for medical devices.

These and other advantages are satisfied, at least in part, by composition for forming a silicone elastomer, the composition comprising: (A) an organopolysiloxane having silicon-bonded alkenyl groups; (B) an organohydrogensiloxane having an average of two or more silicon-bonded hydrogen atoms in the molecule; (C) an inorganic filler; and (D) a filler treatment agent which includes an alkenyl-containing group. While the filler treatment agent having alkenyl groups and inorganic filler can be included in the composition as separate components, a silicone elastomer composition of the present disclosure can advantageously include (C1) an inorganic filler having alkenyl groups instead of or in addition to the inorganic filler and treatment agent as separate components. The compositions can further include (E) a catalytically effective amount of an addition reaction catalyst and/or a curing retarder.

Embodiments include one or more of the following features individually or combined. For example, some embodiments include where the inorganic filler includes fumed silica having a BET specific surface area in a range of about 100 square meters per gram or greater, e.g., about 100 to 400 square meters per gram, which can account for about 30 weight % or more of the total quantity of component (C). In other embodiments, the filler treating agent can be a mixture of (D1) an alkenyl-free organosilane, organosilazane, organosilanol, alkoxyorganosilane, or any combination thereof and (D2) an alkenyl-containing organosilane, organosilazane, organosilanol, alkoxyorganosilane, or any combination thereof, e.g., the filler treating agent can be a mixture of (D1) alkenyl-free organosilane or organosilazane and (D2) alkenyl-containing organosilane or organosilazane. In still further embodiments, the weight ratio of D1/D2 is from about 99/1 to about 50/50.

Another aspect of the present disclosure includes methods of preparing a silicone elastomer. The methods include curing a silicone elastomer composition of the present disclosure and can include compression, transfer or injection molding the composition and/or dip or spray coating the composition on to a substrate and curing the composition to form a cured silicone elastomer.

Another aspect of the present disclosure includes a silicone elastomer having: (i) a Shore-A hardness of from about 20 to about 45 as measured in accordance with ASTM D2240 using a type A durometer hardness tester; (ii) a breaking elongation of at least about 800% as measured in accordance with ASTM D412; and (iii) a tensile strength of at least about 15.0 MPa. In an embodiment of the present disclosure, the silicone elastomer is prepared from the silicone elastomer compositions described herein.

Another aspect of the present disclosure includes medical devices that incorporate the silicone elastomer of the present disclosure. Such medical devices include, for example, a tissue expander, a gastric restriction or gastric balloon, a drug delivery reservoir or dispensing device, a prosthetic device such as a breast implant. As a prosthetic device, the silicone elastomer of the present disclosure can be included as a shell or a component of a shell of the device. Such devices typically also include a filler, such as a silicone gel, a water containing medium such as an aqueous solution, e.g., saline, a composite, a gas such as air, etc.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention.

DETAILED DESCRIPTION OF THE DISCLOSURE

The present disclosure relates to an addition-curable silicone elastomer composition that can be cured to a silicone elastomer product. The cured silicone elastomer can have appropriate properties for use in an implantable or non-implantable medical device, for example. In addition, the present disclosure advantageously relates to a molded cured product of said silicone elastomer composition as part of a medical device, such as a breast implant, medical balloon or medical tube.

The silicone elastomer composition of the present disclosure can be cured to a product having a hardness, as measured in accordance with ASTM D2240 using a type A durometer hardness tester (hereinafter referred to as "Shore-A hardness" or "hardness"), of from about 20 to about 45, having a breaking elongation of 800% or greater and able to avoid the risk of breakage when formed into a shape due to exhibiting excellent tensile strength of more than 15.0 MPa. The silicone elastomer can also have good tearing strength, which is particularly useful for forming a medical pump tube or an implantable or non-implantable medical device as well as low modulus (low stress over a large range of strain values), low tensile set, favorable compression set, and low hysteresis. Such properties are advantageous when using the silicone elastomer as part of various medical devices, for example.

In one aspect of the present disclosure, a silicone elastomer composition includes: (A) an organopolysiloxane having silicon-bonded alkenyl groups; (B) an organohydrogensiloxane having an average of two or more silicon-bonded hydrogen atoms in the molecule; (C) an inorganic filler; and (D) at least one, and preferably a mixture of, filler treatment agents. The composition can further include (E) a catalytically effective amount of an addition reaction catalyst or the catalyst can be provided to the composition including components (A) through (D) at a later time. When the composition includes the catalyst (E), it is preferable to further include a curing retarder (i.e., inhibitor).

It was surprisingly discovered that including a filler treatment agent having alkenyl groups, e.g., vinyl groups, in a silicone elastomer composition produced a cured silicone elastomer with superior properties. It is believed that a filler treatment agent having alkenyl groups produces an inorganic filler having alkenyl groups which are available for chemically reacting with other components in the composition, such as the organohydrogensiloxane. It is further believed that such an inorganic filler can be chemically incorporated into the polymeric network of the cured silicone elastomer which leads to the improved properties of the product.

While the filler treatment agent having alkenyl groups and inorganic filler can be included in the composition as separate components, a silicone elastomer composition of the present disclosure can include (C1) an inorganic filler having alkenyl groups instead of or in addition to the inorganic filler and treatment agent as separate components. In another aspect of the present disclosure, a silicone elastomer composition includes: (A) an organopolysiloxane having silicon-bonded alkenyl groups; (B) an organohydrogensiloxane having an average of two or more silicon-bonded hydrogen atoms in the molecule; and (C1) inorganic filler having alkenyl groups. The composition can further include (E) a catalytically effective amount of an addition reaction catalyst or the catalyst can be provided to the composition including components (A) through (C1) at a later time. When the composition includes the catalyst (E), it is preferable to further include a curing retarder (i.e., inhibitor).

The (C1) inorganic filler having alkenyl groups can be prepare by combining (C) an inorganic filler with (D) a filler treatment agent, e.g., at least one alkenyl-containing organosilane, organosilazane, organosilanol, alkoxyorganosilane, or any combination thereof. Preferably, (C1) is prepared by combining (C) an inorganic filler with a mixture of treatment agents, which can include: (D1) alkenyl-free organosilane, organosilazane, organosilanol, alkoxyorganosilane, or any combination thereof and (D2) alkenyl-containing organosilane, organosilazane, organosilanol, alkoxyorganosilane, or any combination thereof. In an embodiment of the present disclosure, the inorganic filler includes fumed silica and the filler treating agent includes a mixture of an alkyl silazane and an alkenyl containing silazane and the (C1) inorganic filler having alkenyl groups is prepared from fumed silica and the mixture of filler treating agents.

The components of the silicone elastomer composition of the present disclosure are generally in amounts of about (A) 100 parts by weight of an organopolysiloxane having silicon-bonded alkenyl groups; (B) about 0.3 to about 20 parts of an organohydrogensiloxane having an average of two or more silicon-bonded hydrogen atoms in the molecule; (C) about 10 to about 50 parts by weight of an inorganic filler; and (D) about 0.05 to about 20 parts of a filler treatment agent which includes an alkenyl-containing organosilane or organosilazane. In an embodiment of the present disclosure, the composition includes (D) at about 2 to about 8 parts. Alternatively, a silicone elastomer composition can include 100 parts of component (A); about 0.3 to about 20 parts of component (B); and about 10 to about 50 parts of an inorganic filler having alkenyl groups (C1). The parts by weight of the composition for components (A), (B), (C), (C1) and (D) refer to the parts by weight relative to component (A). The composition can further include (E) a catalytically effective amount of an addition reaction catalyst and/or a curing retarder.

In an embodiment of the present disclosure, a silicone elastomer composition includes: (A) 100 parts by weight of an organopolysiloxane having silicon-bonded alkenyl groups, preferably component (A) exhibits a raw rubber state or gum state at room temperature and has a number-average degree of polymerization of 2,000 or greater based on the number average molecular weight in terms of polystyrene equivalent as measured by gel permeation chromatography (GPC), and an average of two or more silicon-bonded alkenyl groups on the organopolysiloxane and an alkenyl group content of less than 0.10 weight %; (B) 0.3 to 20 parts of an organohydrogensiloxane having an average of two or more silicon-bonded hydrogen atoms in the molecule; (C) 10 to 50 parts by weight of an inorganic filler; and (D) 0.05 to 20 parts of a filler treatment agent which includes a mixture of (D1) an alkenyl-free organosilane, organosilazane, organosilanol, alkoxyorganosilane, or any combination thereof and (D2) an alkenyl-containing organosilane, organosilazane, organosilanol, alkoxyorganosilane, or any combination thereof; and (E) a catalytically effective amount of an addition reaction catalyst, e.g., about 0.00001 to about 0.1 parts of an addition reaction catalyst such as platinum based upon the weight ratio of elemental metal to all other components combined.

In another embodiment of the present disclosure, a silicone elastomer composition includes: (A) 100 parts by weight of an organopolysiloxane having silicon-bonded alkenyl groups; (B) 0.3 to 20 parts of an organohydrogensiloxane having an average of two or more silicon-bonded hydrogen atoms in the molecule; and (C1) 10 to 50 parts of inorganic filler having alkenyl groups.

The compositions of the present disclosure include a component (A), which makes-up the largest amount by weight of the composition. As such, component (A) can be a characterizing component that realizes the physical properties of the composition. In an embodiment of the disclosure, component (A) is an organopolysiloxane which exhibits a raw rubber state or gum state at room temperature, contains silicon-bonded alkenyl groups, and has a low content of silicon-bonded alkenyl groups.

Component (A) is an organopolysiloxane which preferably has a number-average degree of polymerization of 2,000 or greater based on the number-average molecular weight in terms of standard polystyrene equivalent as measured by gel permeation chromatography (GPC) (hereinafter referred to as "number-average degree of polymerization"), and which exhibits a raw rubber state or gum state at room temperature. Moreover, it is possible and preferable to reduce the concentrations of low molecular weight siloxanes from these components (A) in advance by using a publicly known means such as stripping.

The organopolysiloxane can include siloxane units having hydrocarbon groups R, (e.g., —SiOR$_2$—) where each R can be the same or different and are substituted or unsubstituted monovalent hydrocarbon groups. Such R groups can have from 1 to 10 carbons, and preferably from 1 to 8 carbons.

Examples of the substituted or unsubstituted monovalent hydrocarbon groups bonded to silicon atoms represented by R include alkyl groups such as methyl groups, ethyl groups, propyl groups, isopropyl groups, butyl groups, isobutyl groups, tert-butyl groups, pentyl groups, neopentyl groups, hexyl groups, cyclohexyl groups, octyl groups, nonyl groups and decyl groups; aryl groups such as phenyl groups, tolyl groups, xylyl groups and naphthyl groups; aralkyl groups such as benzyl groups, phenylethyl groups and phenylpropyl groups; alkenyl groups such as vinyl groups, allyl groups, propenyl groups, isopropenyl groups, butenyl groups, hexenyl groups, cyclohexenyl groups and octenyl groups; groups obtained by substituting some or all of the hydrogen atoms in the aforementioned groups with halogen atoms such as fluorine atoms, bromine atoms and chlorine atoms, cyano groups and the like, such as chloromethyl groups, chloropropyl groups, bromoethyl groups, trifluoropropyl groups and cyanoethyl groups, but it is preferable for 90% or more of the R groups to be methyl groups.

Component (A) can be an organopolysiloxane which has a number-average degree of polymerization of 2,000 or greater, has an average of two or more silicon-bonded alkenyl groups, and exhibits a raw rubber state or gum state at room temperature. In terms of the structure of this component, the content of silicon-bonded alkenyl groups is determined according to the degree of polymerization and the presence/absence of branches on the main chain, but component (A) is preferably a straight chain or partially branched organopolysiloxane in which the alkenyl group content is from 0.001 to 0.1 weight %, and more preferably a straight chain organopolysiloxane having an average of two or more silicon-bonded alkenyl groups at both molecular termini.

In an aspect of the present disclosure, the structure of component (A) is such that the molecular termini are capped by triorganosiloxy groups having silicon-bonded alkenyl groups and the main chain has a straight chain structure comprising repeating diorganosiloxane units, but may be a partially branched chain structure. The molecular weight of component (A) is such that the number-average degree of polymerization is 2,000 or greater (from 2,000 to 100,000) and component (A) exhibits in a raw rubber state or gum state, and the number-average degree of polymerization is preferably 3,000 or greater (from 3,000 to 8,000). If the number-average degree of polymerization is less than the aforementioned lower limit, it is difficult to obtain a satisfactory rubbery feeling, the surface may become sticky or tacky.

The organopolysiloxane of component (B) is a crosslinking agent for the present composition, and is an organopolysiloxane having an average of two or more silicon-bonded hydrogen atoms in the molecule. The bonding sites of the silicon-bonded hydrogen atoms in component (B) are not particularly limited, and may be molecular termini, or pendant to (along) the molecular chains or molecular termini and pendant to the molecular chains. In addition, examples of silicon-bonded groups other than hydrogen atoms in component (B) include monovalent hydrocarbon groups, for example, alkyl groups such as methyl groups, ethyl groups, propyl groups, butyl groups, pentyl groups and hexyl groups; cycloalkyl groups such as cyclopentyl groups and cyclohexyl groups; aryl groups such as phenyl groups, tolyl groups and xylyl groups; aralkyl groups such as benzyl groups and phenethyl groups; halogenated alkyl groups such as 3,3,3-trifluoropropyl groups and 3-chloropropyl groups; alkenyl groups such as vinyl groups, allyl groups, propenyl groups, isopropenyl groups, butenyl groups, hexenyl groups, cyclohexenyl groups and octenyl groups, with alkyl groups and aryl groups being preferred and methyl groups and phenyl groups being particularly preferred.

The molecular structure of component (B) is not limited, and may be, for example, straight chain, branched chain, straight chain having some branches, cyclic, dendritic (dendrimer-like) or resin-like. Component (B) may be a homopolymer having these molecular structures, a copolymer comprising these molecular structures or a mixture thereof.

The viscosity of component (B) is not limited, but the viscosity at 25° C. (as measured using a rotational viscometer and the like) is preferably from 1 to 100,000 mPa–s, more preferably from 1 to 10,000 mPa–s, and particularly preferably from 1 to 5,000 mPa–s.

Examples of this type of component (B) include methylhydrogenpolysiloxanes capped at both molecular termini with trimethylsiloxy groups, copolymers of dimethylsiloxane and methyl hydrogen siloxane capped at both molecular termini with trimethylsiloxy groups, dimethylpolysiloxane capped at both molecular termini with dimethylhydrogensiloxy groups, methylhydrogenpolysiloxanes capped at both molecular termini with dimethylhydrogensiloxy groups, copolymers of dimethylsiloxane and methyl hydrogen siloxane capped at both molecular termini with dimethylhydrogensiloxy groups, cyclic methylhydrogenpolysiloxanes, organosiloxanes comprising siloxane units represented by the formula $(CH_3)_3SiO_{1/2}$, siloxane units represented by the formula $(CH_3)_2HSiO_{1/2}$ and siloxane units represented by the formula $SiO_{4/2}$, tetra(dimethylhydrogensiloxy)silanes and methyltri(dimethylhydrogensiloxy)silanes.

In the present composition, the content of component (B) is from 0.1 to 20 parts by weight per 100 parts by weight of component (A), and is preferably such that the amount of silicon-bonded hydrogen atoms in component (B) is from 1.0 to 20 moles, more preferably from 1.0 to 10 moles, and particularly preferably from 1.0 to 6 moles, per 1 mole of silicon-bonded alkenyl groups in component (A). This is because if the content of component (B) is less than the lower limit of the above-mentioned range, crosslinking is inadequate, the hardness of the obtained cured silicone elastomer product is insufficient, the surface may become sticky or tacky. Meanwhile, if the content of component (B) exceeds the upper limit of the above-mentioned range, hydrogen gas is generated from the obtained cured silicone elastomer product, foaming occurs in a molded product, and it may be difficult to release a molded product from a mold. A preferred compounded amount of component (B) is from 0.1 to 10 parts weight, and especially from 0.1 to 5 parts by weight, per 100 parts by weight of component (A).

Component (C) is an inorganic filler, which imparts the silicone elastomer with strength, among other properties. The filler is not limited so long as the filler imparts the silicone elastomer with hardness and permanent elongation, as described below. It is possible to use one or more types of inorganic filler, and component (C) can be a reinforcing filler such as a silica fine powder or fumed titanium oxide; a non-reinforcing filler such as diatomaceous earth, an aluminosilicate, iron oxide, zinc oxide or calcium carbonate; or a thermally conductive filler such as aluminum oxide or boron nitride. A silica fine powder can be a dry type silica such as fumed silica or a synthetic silica such as a wet type silica, and preferably has a specific surface area, as measured using the BET method, of about 100 square meters per gram or greater, and more preferably from 100 to 400 square meters per gram such as from about 130 to 350 square meters per gram, such as from about 200 to about 325 square meters per gram. In an embodiment of the present disclosure, the inorganic filler includes fumed silica which accounts for at least 30 weight % of the total quantity of component (C), e.g. the inorganic filler includes 50 weight % or more, 80 weight % or more of the total quantity of component (C).

In addition, the compounded amount of the inorganic filler of component (C) is from 10 to 100 parts by weight, and preferably from 10 to 50 parts by weight, e.g., from 25 to 35 parts by weight, per 100 parts by weight of component (A). It is difficult to achieve satisfactory hardness or physical strength if the compounded amount is less than the aforementioned lower limit, and elasticity deteriorates, tensile strength and breaking elongation in particular deteriorate, and the composition may not be suitable for use as a medical device if the compounded amount exceeds the aforementioned upper limit.

The inorganic filler of component (C) (for example, fumed silica) can be used without further modification, but can also be treated in advance with a surface treatment agent, such as component (D), to form an inorganic filler having alkenyl groups. Examples of surface treatment agents are provided below for component (D).

Component (D) is a surface treatment agent for the inorganic filler which includes an alkenyl-containing group. Examples of such a filler treatment agent include an alkenyl-containing organosilane, organosilazane, organosilanol, alkoxyorganosilane, or any combination thereof. In one aspect of the present disclosure, the filler treatment agent, component (D), is a mixture of (D1) alkenyl-free organosilane, organosilazane, organosilanol, alkoxyorganosilane, or any combination thereof and (D2) alkenyl-containing organosilane, organosilazane, organosilanol, alkoxyorganosilane, or any combination thereof, e.g., a mixture of (D1) alkenyl-free organosilane or organosilazane and (D2) alkenyl-containing organosilane or organosilazane. For example, the filler treating agent can include a mixture of D1 an organosilane or organosilazane including alkyl, aryl, haloalkyl or haloaryl groups and 0 weight % alkenyl functional groups, e.g., a silane, chlorosilane, silazane, an alkyl substituted silane, chlorosilane, silazane, and (D2) an organosilane or organosilazane including alkenyl functional groups or both (i) alkyl (e.g., $C_{1-8}$ alkyl), aryl, haloalkyl or haloaryl and (ii) alkenyl functional groups, e.g., a $C_{1-8}$ alkyl, aryl, haloalkyl or haloaryl and vinyl substituted silane or silazane. The mixture can include a weight ratio of D1/D2 of from about 99/1 to about 50/50 and preferably from about 99/5 to about 80/20, e.g., from about 92/8 to about 88/12. In an embodiment of the present disclosure, D1 and D2 have a parts by weight ratio (D1:D2) of from about 15:1 to about 5:1.

As explained above, it is believed that the alkenyl groups formed on the inorganic filler can chemically react, e.g., to form covalent bonds, with other components in the composition to form a chemically bound filler incorporated in the cured silicone elastomer. The structure or "architecture" of other parts of this network is also a consideration and includes the polymer-to-polymer crosslinking and non-covalent polymer-to-silica interactions (primarily surface wetting and hydrogen bonding) in addition to the covalent polymer-to-silica bonds. The balance of these factors provides the ultimate and desired properties of the silicone elastomer of the present disclosure. As shown in the examples below, compositions that included a filler treatment agent with alkenyl groups (Examples 1-4) provided superior tensile strength over a comparable example that included a filler treatment agent but without alkenyl groups (Comparative Example 1).

The addition reaction catalyst of component (E) is a catalyst used to facilitate curing of the present composition, and may be a platinum-based catalyst, a palladium-based catalyst, a rhodium-based catalyst and the like. A platinum metal-type catalyst is particularly preferred.

Examples of component (E) include platinum-based catalysts, for example, platinum fine powders, platinum black, chloroplatinic acid, platinum tetrachloride, alcohol-modified chloroplatinic acid, olefin complexes of platinum, alkenyl-siloxane complexes of platinum, carbonyl complexes of platinum, carbene complexes of platinum, platinum on finely divided solid supports such as silica, powdered thermoplastic organic resins and silicone resins containing these platinum-based catalysts; rhodium-based catalysts, palladium based catalysts, other transition metal based catalysts.

The content of component (E) in the present composition is a catalytic quantity, but is more specifically an amount where the quantity of a platinum group metal in component (E) is from 0.01 to 1,000 ppm by weight, and preferably from 0.1 to 500 ppm by weight, relative to the total quantity of component (A). This is because the obtained silicone elastomer composition is not sufficiently cured if the content of component (E) is less than the lower limit of the above-mentioned range and the curing speed of the obtained silicone elastomer composition is not significantly improved even if the content of component (E) is greater than the upper limit of the above-mentioned range.

The silicone elastomer composition according to the present disclosure can contain the above-mentioned components (A) to (E), but may also contain (F) an inert solvent.

It is particularly preferable for component (F) to be used where the end-use product requires a lower viscosity, as is the case for spray or dip-coating the composition on to a substrate, e.g., a medical device. Component (F) is an optional component that may be compounded if necessary, and the compounded amount thereof is greater than 100 parts by weight, and preferably from 100 to 1,000 parts by weight, per 100 parts by weight of component (A).

The addition-curable silicone elastomer composition according to the present disclosure may contain a curing retarder in order to adjust the curing speed or pot life. Examples of curing retarders include alcohol derivatives having carbon-carbon triple bonds, such as 3-methyl-1-butyn-3-ol, 3,5-dimethyl-1-hexyn-3-ol, phenylbutynol and 1-ethynyl-1-cyclohexanol; ene-yne compounds such as 3-methyl-3-penten-1-yne and 3,5-dimethyl-3-hexen-1-yne; alkenyl group-containing low molecular weight siloxanes such as tetramethyltetravinylcyclotetrasiloxane and tetramethyltetrahexenylcyclotetrasiloxane; and alkyne-containing silanes such as methyl-tris(3-methyl-1-butyne-3-oxy)silane and vinyl-tris(3-methyl-1-butyne-3-oxy)silane.

The compounded amount of the curing retarder may be selected as appropriate according to the usage method, molding method and the like of the addition-curable silicone elastomer composition. A commonly used compounded amount is from 0.001 to 5 weight % relative to the total mass of the composition.

The addition-curable silicone elastomer composition according to the present disclosure may contain carbon black such as acetylene black, furnace black or channel black as long as the properties of the elastomer are not impaired. In addition, the addition-curable silicone elastomer composition according to the present disclosure may, if necessary, contain additives such as pigments (coloring agents such as red iron oxide and organic pigments, titanium dioxide and the like), heat-resistant agents, flame retardants, internal release agents, plasticizers, non-functional silicone oils and the like). Moreover, examples of internal release agents include higher fatty acid salts such as calcium stearate. Moreover, it is particularly preferable to use additives such as heat-resistant agents and flame retardants when the addition-curable silicone elastomer composition according to the present disclosure is used as a medical tube in an environment that is exposed to high temperatures, such as in heat sterilization or in a thermocouple.

The silicone elastomer composition of the present disclosure can be readily prepared by homogeneously mixing components (A) through (E) together along with any optional ingredients. Mixing the components and ingredients can be achieved by any conventional means such as a Morehouse Cowles mixer, a two roll mill or a kneader mixer.

The method for molding or curing the addition-curable silicone elastomer composition according to the present disclosure may be a commonly used method, but the molding method is preferably an injection molding method, a compression or transfer molding method, an extrusion molding method (including hot air vulcanization), a dip molding method, a spray molding method, or a rotary molding method. In addition, curing conditions such as the curing temperature and the curing time are not particularly limited, and good curing is generally carried out at a temperature from room temperature to 220° C. From the perspective of industrial production of an elastic material for a medical device such as a medical tube, it is possible to use heat curing conditions of from 80 to 230° C. for a period of from 3 seconds to 60 minutes, and preferably from 100 to 200° C. for a period of from 5 seconds to 30 minutes. In addition, by press curing (compression molding) the addition-curable silicone elastomer composition according to the present disclosure at 150° C. for 10 minutes, as described below, an elastic material for a medical device can exhibit appropriate hardness and permanent elongation characteristics, but it is also possible to cure the composition by means of a stepwise vulcanization (step curing) process, such as carrying out primary vulcanization and then carrying out secondary vulcanization. In such cases, however, the cycle time required for production may be increased and productivity may decrease.

Specifically, the addition-curable silicone elastomer composition according to the present disclosure can be cured in a single step at the above-mentioned temperatures. Furthermore, characteristics such as permanent elongation may be further improved by step curing in which the composition is first heated to a temperature from room temperature to 150° C., and preferably from 60 to 150° C., and then heated to from 80 to 200° C., and preferably from 100 to 180° C. In addition, in order to remove small quantities or trace quantities of volatile components and further improve characteristics such as permanent elongation, it is preferable to carry out secondary vulcanization (heat aging) at from 150 to 250° C. for a period of from 10 minutes to 8 hours following completion of the curing.

By having the constitution described above, the addition-curable silicone elastomer composition according to the present disclosure is characterized by providing a cured product having a hardness, as measured in accordance with ASTM D2240 using a type A durometer hardness tester (Shore-A hardness), of from about 20 to about 45. The Shore-A hardness is preferably from 25 to 45. If the hardness falls outside the aforementioned range, the strength and flexibility of the cured product may be insufficient and the cured product may not be suitable for use as a medical device.

Furthermore, the cured product of the addition-curable silicone elastomer composition according to the present disclosure has a tensile strength, as specified in ASTM D412, of about 15.0 MPa or greater, more preferably from about 15.0 to about 21.0 MPa, and particularly preferably from about 17.0 to about 21.0 MPa.

In addition, from the perspective of strength as an elastic material for a medical device, the cured product has a breaking elongation, as specified in ASTM D412, of about 800% or greater, and preferably from about 800 to about 1,300%. Moreover, the breaking elongation is preferably from about 800 to about 1,000% when the aforementioned hardness is from 35 to 45, and more preferably from about 800 to about 1,200% when the aforementioned hardness is from about 20 to about 35.

Physical properties such as the above-mentioned hardness, breaking elongation, and tensile strength are physical properties that are achieved as a direct result of the constitution of the addition-curable silicone elastomer composition according to the present disclosure, and especially as a result of using the prescribed components (A), (B), (C) and (D) or (A), (B) and (C1). Furthermore, from the perspective of use as an elastic material for a medical device such as a medical tube, the addition-curable silicone elastomer composition according to the present disclosure has a 100% modulus (M100), as measured in accordance with ASTM D412, of from 0.30 to 5.0 MPa, and particularly preferably from 0.3 to 2 MPa, following press curing at 150° C. for 10 minutes.

Similarly, from the perspectives of strength and service life as an elastic material for a medical device, the addition-curable silicone elastomer composition according to the present disclosure preferably has a tearing strength, as measured in accordance with ASTM D684 using a crescent mold, of 30 kN/m or more, and especially from 30 to 50 kN/m.

Another aspect of the present disclosure includes medical devices that incorporate the silicone elastomers of the present disclosure. The silicone elastomer of the present disclosure can be a component part of a medical device that functions as a tissue expander, a gastric restriction or gastric balloon, an artificial urethral sphincter, a drug delivery reservoir or dispensing device, a prosthetic device such as a breast implant, a testicular prosthesis, a penile prosthesis, a calf prosthesis, a buttocks prosthesis, a vitreous body prosthesis in the eye, an inflatable facial prosthesis. The silicone elastomer of the present disclosure can also be used as a component of an implantable mechanical device such as a valve, finger joint or toe joint. The silicone elastomer of the present disclosure can be a coating or part thereof for a medical device such as a stent, housing for electronic device such as a pacemaker, or a mechanical device such as a pressure transducer or strain gauge or on a catheter, or as a drain or pump tubing.

As a prosthetic device, the silicone elastomer of the present disclosure can be included as a shell or a component of a shell of the device. Such devices typically also include a filler, such as a silicone gel, a water containing medium such as an aqueous solution, e.g., saline, a composite, a gas such as air. The shell typically envelopes the filler and can further include components to seal the filler in the shell such as patches, valves or sealants to establish a continuous barrier to contain the filler material. In an embodiment, a medical device comprises an outer shell including the silicone elastomer of the present disclosure, e.g., a prosthetic such as a breast implant. The medical device, e.g., prosthetic such as a breast implant, can further include a filler material, e.g., a silicone gel or a water containing medium such as saline.

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Measurement of number-average molecular weight and average degree of polymerization. In the Examples and the like, the average degree of polymerization of an organopolysiloxane is the number-average degree of polymerization, based on the number-average molecular weight relative to polystyrene equivalent as measured by gel permeation chromatography (GPC) using an analytical apparatus described below, and was measured under the following conditions: Measurement temperature: 35° C. (column oven temperature); Sample: 1 weight % toluene solution of organopolysiloxane; Detector: Refractive index detector; Polymer for calibration curve: Standard polystyrene.

GPC separations were performed on an Agilent 1260 Infinity HPLC system with refractive index (RI) detector and ChemStation software. Two Phenomenex Phenogel fixed pore GPC columns (300×7.8 mm) were connected in series: Injector—Phenogel 10,000 A—Phenogel 500 A—Detector. The mobile phase was toluene at a flow rate of 1.0 mL/minute. Columns were maintained at a temperature of 35 C.

Components. The components used in the Examples and Comparative Example, as reported in Table 1 below, were as follows: (A) Organopolysiloxane 1 (gum-like state) Dimethylsiloxane capped at both molecular termini with vinyldimethylsilyl groups (number-average degree of polymerization: 3,290) (Commercially available from NuSil catalogue No. MED-4502); (B) Organohydrogenpolysiloxane Copolymer of dimethylsiloxane and methyl hydrogen siloxane capped at both molecular termini with trimethylsilyl groups (viscosity: 5.2 mPa–s, Si—H content: 7.2 mmol Si—H/gram, 50% methylhydrogen units per molecule. (Commercially available from NuSil catalogue No. XL-110); (C) Fumed silica having a BET specific surface area of 200 square meters per gram, purchased from Cabot Corporation; (D1) hexamethyldisilazane, available from multiple sources including Sigma Aldrich, which acted as a filler treating agent containing alkyl (methyl) groups and 0 weight % alkenyl functional groups on an organosilane; (D2) symmetrical-tetramethyldivinyldisilazane, available from multiple sources including Sigma Aldrich, which acted as a filler treating agent containing both alkyl (methyl) and alkenyl (vinyl) functional groups on an organosilane; (E) Addition reaction catalyst Platinum-1,3-divinyl-,1,3,3-tetramethyldisiloxane complex. (The amount of elemental platinum used in the composition was 5 parts per million by weight relative to the total silicone elastomer composition); (F) xylenes which acted as a medium to disperse the components of the composition. The curing retarder was 1-ethynyl-1-cyclohexanol.

TABLE 1

| | Examples | | | | Comparative |
|---|---|---|---|---|---|
| | Example #1 | Example #2 | Example #3 | Example #4 | Example #1 |
| Component | | | | | |
| (A) | 73.71% | 69.84% | 78.03% | 19.59% | 78.18% |
| (B) | 0.27% | 0.27% | 0.27% | 0.11% | 0.27% |
| (C) | 23.40% | 26.89% | 19.51% | 6.22% | 19.55% |
| (D1) | 2.34% | 2.69% | 1.95% | 0.62% | 1.95% |
| (D2) | 0.23% | 0.27% | 0.20% | 0.06% | 0.00% |
| (E) | 0.02% | 0.02% | 0.02% | 0.01% | 0.02% |
| (F) | 0.00% | 0.00% | 0.00% | 73.39% | 0.00% |
| Curing Retarder | 0.02% | 0.02% | 0.02% | 0.01% | 0.02% |
| SiH/Vi Ratio | 2.3 | 2.3 | 2.3 | 2.3 | 2.3 |
| Physical Properties | | | | | |
| Type A Hardness | 30 | 35 | 25 | 39 | 22 |
| Tensile Strength (MPa) | 17.4 | 17.2 | 17.7 | 18.9 | 11.7 |
| 100% Modulus (MPa) | 0.47 | 0.54 | 0.43 | 0.59 | 0.35 |
| Breaking Elongation (%) | 1,123 | 1,033 | 1,155 | 989 | 1,218 |
| Tear Strength (kN/m) | 44.7 | 47.2 | 42.6 | 37.4 | 41.4 |

The components listed in Table 1 are in weight percent.

Sample preparation and curing conditions. For Examples 1 to 3 and Comparative Example 1, components A, C and D reported in Table 1 were combined in a mixer with constant agitation at a temperature of 80° C. for a minimum of 30 minutes and then subjected to vacuum at a temperature of 160° C. for a minimum of 3 hours. After cooling this "base" compound was split into two parts. Component E was added to the first part on a two-roll mill to produce Part A. Component B and cure retarder were added to the second part on a two-roll mill to produce Part B. Part A and Part B were homogeneously mixed on a two roll mill and then press vulcanized at 150° C. for 10 minutes to obtain samples having thicknesses of about 2 mm. For Example 4, which is an example of a dispersion composition including xylenes (component (F)), the components reported in Table 1 were mixed as above and then Part A and Part B were separately dispersed in xylenes. Part A and Part B dispersions were mixed and cast into a non-stick mold, and the mixture was cured to give an elastomer slab of 0.75 mm thickness in a class-A oven with the following ramp cure schedule:

60 minutes at 50° C.
60 minutes at 75° C.
180 minutes at 150° C.

Example 4 is an example of using a silicone elastomer composition in the form of a dispersion or solution to produce a coated medical device (especially medical implant shells) by dip or spray coating the composition onto the device and then curing.

The following physical properties of the cured silicone elastomeric products of Examples 1 to 4 and Comparative Example 1 were measured in the following manner.

(1) Type A hardness: The hardness of a cured silicone elastomer sample was measured in accordance with ASTM D2240 (Standard Test Method for Rubber Property—Durometer Hardness) (Type A hardness, measured using a Shore type A durometer).

(2) Tensile strength, 100% modulus: Measured in accordance with ASTM D412 (Standard Test Methods for Vulcanized Rubber and Thermoplastic Elastomers—Tension) using a Universal Test System manufactured by MTS Systems Corporation. Moreover, the tensile stress at 100% elongation was recorded as the 100% modulus.

(3) Tear strength: A crescent shaped sample as described in ASTM D684 (Standard Test Method for Tear Strength of Conventional Vulcanized Rubber and Thermoplastic Elastomers) was cut out from the above-mentioned elastomers and used as a sample. Using this sample, the tearing strength was measured in accordance with ASTM D684 using a Universal Test System manufactured by MTS Systems Corporation.

(4) Breaking elongation: This was measured in accordance with ASTM D412 using a Universal Test System manufactured by MTS Systems Corporation, and the elongation at the point where the sample broke was expressed as a proportion (%) relative to the initial value.

As shown in Table 1, the compositions of Examples 1 to 3 were cured to form silicone elastomers which had hardness of from 25 to 35, high breaking elongation of greater than 1,000% and high tensile strength of greater than 17.0 MPa. Example 4 provided a silicone elastomer which had a hardness of 39, a high breaking elongation of over 900% and had high tensile strength of greater than 18.0 MPa. Such silicone elastomers can be prepared by a dip- or spray-coated process and suitable for medical devices (especially medical implant shells).

As shown in Table 1, Comparative Example 1 had inferior tensile strength (less than 12.0 MPa) and inferior hardness (less than 25). Comparative Example #1 demonstrates that leaving out a filler treatment agent having alkenyl groups in the composition results in a silicone elastomer with significantly worse properties despite the fact that a filler treatment agent was included in the composition. This Comparative Example demonstrates the significance of the filler treatment agent having alkenyl groups.

As shown in Table 1, Examples 1-4 were silicone elastomer compositions that included a filler treatment agent having alkenyl groups. By using the silicone elastomer compositions of Examples 1 to 4, it was possible to obtain a cured product having physical properties appropriate for an elastic medical material. In particular, the cured products of Examples 1 to 4 had particularly high tensile strength and tear strength and are therefore highly suitable for use as an implantable medical device.

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

What is claimed is:

1. A silicone elastomer made by the process comprising:
   (1) forming a composition, the composition comprising:
      (A) 100 parts of an organopolysiloxane having alkenyl radicals,
      (B) 0.1 to 5 parts of an organohydrogensiloxane having an average of two or more silicon-bonded hydrogen atoms in the molecule,
      (C) 10 to 50 parts of an inorganic filler, and
      (D) 2 to 8 parts of a filler treatment agent which includes an alkenyl-containing group; and
   (2) curing the composition to form a silicone elastomer having:
      (i) a Shore-A hardness of from about 20 to about 45 as measured in accordance with ASTM D2240 using a type A durometer hardness tester;
      (ii) a breaking elongation of at least about 800% as measured in accordance with ASTM D412; and
      (iii) a tensile strength of at least 15.0 MPa.

2. The silicone elastomer of claim 1, further comprising in the composition (E) a catalytically effective amount of an addition reaction catalyst.

3. The silicone elastomer of claim 1, further comprising in the composition a cure retarder.

4. The silicone elastomer of claim 1, wherein the inorganic filler includes fumed silica having a BET specific surface area in a range of about 100 square meters per gram or greater which accounts for 30 weight % or more of the total quantity of component (C).

5. The silicone elastomer of claim 1, wherein the filler treating agent includes a mixture of (D1) an alkenyl-free organosilane or organosilazane and (D2) an alkenyl-containing organosilane or organosilazane.

6. The silicone elastomer of claim 5, wherein D1 and D2 have a parts by weight ratio (D1:D2) of from about 15:1 to about 5:1.

7. The silicone elastomer of claim 6, wherein D1 is an alkyl substituted silazane and D2 is a vinyl substituted silazane.

8. The silicone elastomer of claim 1, further comprising combining the composition with a solvent to form a dispersion or solution of the composition prior to curing the composition.

9. The silicone elastomer of claim 1, further comprising dip or spray coating the composition on to a substrate and curing the composition to form a cured silicone elastomer.

10. A medical device including the silicone elastomer of claim 1.

11. A medical device comprising an outer shell including the silicone elastomer of claim 1.

12. The medical device of claim 11, further including a filler material selected from a silicone gel or a water containing medium.

13. The medical device of claim 12 which is a breast implant.

14. The silicone elastomer of claim 1, wherein the inorganic filler is present in the composition in 25 to 50 parts.

15. The silicone elastomer of claim 1, wherein curing occurs at a temperature of 80-230° C. for 3 seconds to 60 minutes.

16. The silicone elastomer of claim 15, wherein curing occurs at a temperature of 150° C. for 10 minutes.

* * * * *